US010813596B1

(12) United States Patent
Sarraf et al.

(10) Patent No.: US 10,813,596 B1
(45) Date of Patent: Oct. 27, 2020

(54) METHODS AND SYSTEMS FOR DETECTING POTENTIAL INJURY CONDITIONS

(71) Applicant: American International Group, Inc., New York, NY (US)

(72) Inventors: Mohsen Sarraf, Rumson, NJ (US); Christopher Michael Bunk, Norwalk, NJ (US); Sergey Vikhlyantsev, New York, NY (US); Jennifer A. Martinez, Newark, NJ (US)

(73) Assignee: American International Group, Inc., New York, NY (US)

( * ) Notice: Subject to any disclaimer, the term of this patent is extended or adjusted under 35 U.S.C. 154(b) by 579 days.

(21) Appl. No.: 15/639,339

(22) Filed: Jun. 30, 2017

Related U.S. Application Data

(60) Provisional application No. 62/372,100, filed on Aug. 8, 2016.

(51) Int. Cl.
*A61B 5/00* (2006.01)
*A61B 5/11* (2006.01)

(52) U.S. Cl.
CPC .......... *A61B 5/7275* (2013.01); *A61B 5/0004* (2013.01); *A61B 5/1121* (2013.01); *A61B 5/6804* (2013.01); *A61B 5/742* (2013.01); *A61B 5/7475* (2013.01); *A61B 2562/0219* (2013.01)

(58) Field of Classification Search
CPC ... A61B 5/7275; A61B 5/6804; A61B 5/7475; A61B 5/1121; A61B 5/742; A61B 5/0004; A61B 2562/0219
See application file for complete search history.

(56) References Cited

U.S. PATENT DOCUMENTS

| 2007/0250286 | A1* | 10/2007 | Duncan | A61B 5/1121 |
| | | | | 702/139 |
| 2011/0179850 | A1* | 7/2011 | Klinnert | A61B 5/1126 |
| | | | | 73/1.37 |
| 2014/0276240 | A1* | 9/2014 | Stein | A61B 5/4851 |
| | | | | 600/595 |
| 2017/0312515 | A1* | 11/2017 | Ferree | A61N 1/0476 |

* cited by examiner

*Primary Examiner* — Eric F Winakur
*Assistant Examiner* — Abid A Mustansir
(74) *Attorney, Agent, or Firm* — Leydig, Voit & Mayer, Ltd.

(57) ABSTRACT

A system includes a sensor attached to an individual and detects an individual's improper body movements that increase injury risk. The system includes a safety tag with an accelerometer that measures proper acceleration. Proper acceleration along multiple directions are projected onto multiple 2-D planes, generating acceleration vectors. Phasor angles of the acceleration vectors are calculated, and if the spread in phasor angles for any one 2-D plane within a moving time window exceeds a threshold, the system determines that the individual has made an improper body movement.

39 Claims, 11 Drawing Sheets

METHODS AND SYSTEMS FOR DETECTING POTENTIAL INJURY CONDITIONS

This application claims priority to provisional Application No. 62/372,100, filed on Aug. 8, 2016, which is incorporated by reference as if fully set forth herein.

BACKGROUND OF THE INVENTION

Field of the Invention

The present invention relates to methods and systems for recognizing potential injury conditions using wearable sensors, including distinguishing between correct and incorrect bending motions based on data from wearable sensor devices.

Description of Related Art

In workplace settings where workers are responsible for physically handling large and/or heavy articles (e.g., construction sites or warehouses), injuries frequently occur when workers place excess strain on their bodies while carrying out their duties. One common injury sustained by workers is a back injury arising from certain body motions while handling physical objects. In particular, the likelihood of a back injury substantially increases when a worker picks up objects by bending at the waist instead of bending at the knees. While bending at the knees is a simple solution to avoid a back injury, many workers fail to either realize this concept or recognize that their bending motion is improper. Therefore, close monitoring of these workers is important for reducing these types of workplace injuries. However, in a large work environment involving hundreds of workers or more, it is difficult to monitor workers' behavior with sufficient attention to prevent incorrect bends. Therefore, a more efficient approach is needed to monitor worker movements, recognize when these movements are problematic, and reduce the possibility of worker injuries.

SUMMARY OF THE INVENTION

One object of the invention relates to a wearable tag containing one or more sensors to measure the movement of the user.

Another object of the invention relates to a system for detecting a potential injury condition, the system comprising a receiver configured to receive sensor data from a sensor worn by an individual, the sensor data containing three-dimensional acceleration information corresponding to movement of the individual; and a processor configured to determine, based on the sensor data, a potential injury condition of the individual.

Yet another object of the invention relates to a method of detecting a potential injury condition, comprising electronically receiving sensor data from a sensor worn by an individual, the sensor data containing three-dimensional acceleration information corresponding to movement of the individual; and electronically determining, using a processor and based on the sensor data, a potential injury condition of the individual.

Still yet another object of the invention relates to a non-transitory computer readable storage medium storing one or more programs, the one or more programs comprising instructions, which, when executed by an electronic device with one or more processors, cause the electronic device to perform the steps of receiving sensor data from a sensor worn by an individual, the sensor data containing three-dimensional acceleration information corresponding to movement of the individual; and determining, based on the sensor data, a potential injury condition of the individual.

A further object of the invention relates to a system for detecting a potential injury condition, comprising a sensor worn by an individual; a receiver configured to receive sensor data from the sensor, the sensor data containing three-dimensional acceleration information corresponding to movement of the individual; and a processor configured to determine, based on the sensor data, a potential injury condition of the individual.

A yet further object of the invention relates to a system, method, or non-transitory computer readable storage medium for determining a potential injury condition using a mechanism that resides in a sensor tag. A still further object of the invention relates to a system, method, or non-transitory computer readable storage medium for determining a potential injury condition using a mechanism that resides in a location remote from a sensor tag.

Further features and advantages, as well as the structure and operation, of various example embodiments of the present invention are described in detail below with reference to the accompanying drawings.

DETAILED DESCRIPTION OF THE INVENTION

Figure 1:
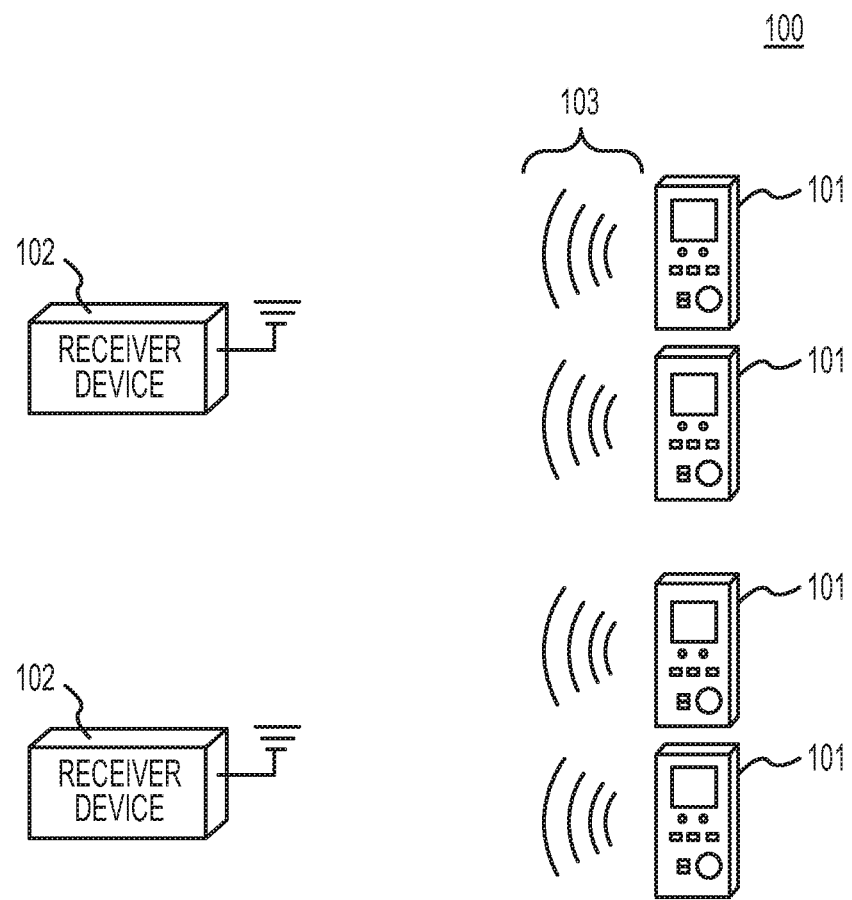
FIG. 1 illustrates a sensor system in accordance with an embodiment of the invention.

FIG. 1 illustrates a sensor system 100 in accordance with an embodiment of the invention. The system 100 includes one or more sensor tag devices 101 being worn by individuals in an operating environment. The sensor tag devices 101 are attached to the individuals. The system 100 also includes one or more receiver devices 102. Each sensor tag 101 communicates with a receiver device 102 over a wireless data connection 103. The wireless data connection 103 preferably allows for two-way communication between the sensor tag 101 and the receiver device 102, but it will be appreciated that the wireless data connection 103 may be configured as providing only one-way communication from the sensor tag 101 to the receiver device 102.

Figure 2A:
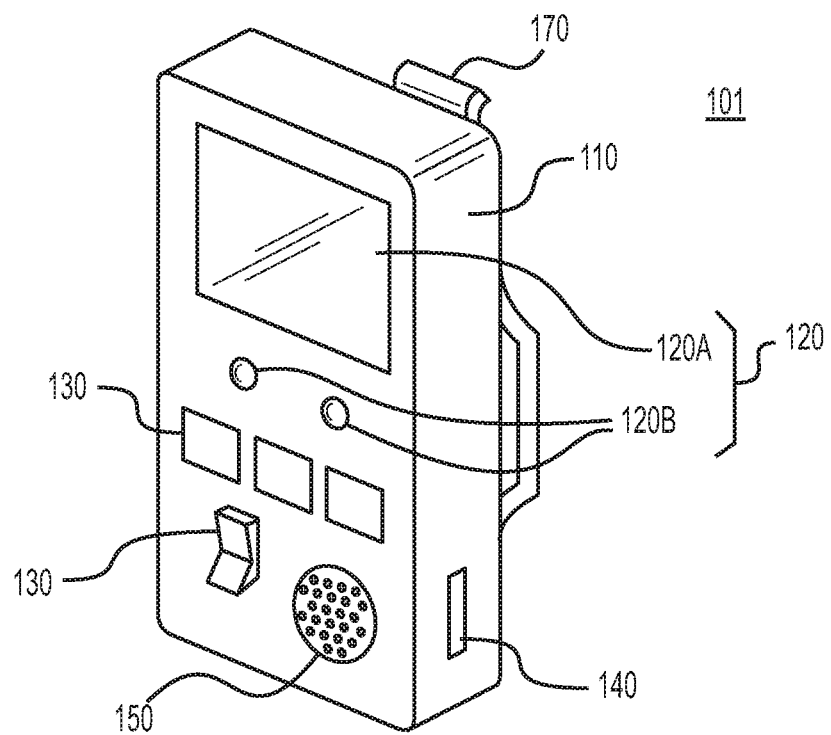
FIG. 2a illustrates a sensor tag in accordance with an embodiment of the invention.

FIG. 2a illustrates a sensor tag 101 in accordance with one embodiment of the invention. External features of the sensor tag 101 includes a housing 110, a visual output section 120, a user input section 130, an interface port 140, an audio input/output section 150, a wireless antenna 160, and an attachment component 170. The sensor tag 101 is attached to a person of interest, such as to their clothing or belt.

The housing 110 encloses the internal components of the sensor tag 101. The housing 110 is preferably made of a durable and lightweight material, such as plastic, but could alternatively be made of other materials such as rubber or metal, or a combination of multiple materials. It will also be appreciated that the housing 110 may be implemented according to a variety of shapes and sizes, depending, for instance, on the particular internal and external components being used, and on the particular manner in which the sensor tag 101 is designed to be retained on a user.

The visual output section 120 provides visual indicators to a user. The visual output section 120 includes one or more components, such as a graphical display 120a displaying text characters or graphics, and one or more light indicators 120b (e.g., LED lights). The graphical display 120a is preferably a monochrome or color LCD display screen, or a series of LCD or LED multi-segment displays (e.g., 7-segment, 14-segment, 16-segment character display). The light indicators 120b are preferably single LED emitters, each controllable to emit one or more colors. It will be appreciated that the graphical display 120a may additionally, or alternatively, include a CSTN (Color Super Twisted Nematic), TFT (Thin Film Transistor), TFD (Thin Film Diode), OLED (Organic Light-Emitting Diode), AMOLED display (Activematrix organic light-emitting diode), electronic paper (e.g., e-book), and/or any other type of graphical display.

The user input section 130 receives inputs from the user, for operating, controlling, and/or adjusting the sensor tag 101. The user input section 130 includes one or more switches, dials, or buttons that the user manipulates to control the sensor tag 101. As an alternative or in addition, the user input section 130 may incorporate a touch-screen interface integrated with the graphical display 120a. In such instance, the touch-screen interface may incorporate a capacitive or resistive-type touch-screen component, but alternatively, can incorporate any other form of touch-screen technology.

The interface port 140 provides a data transfer connection between the sensor tag 101 and another device, and also supplies power to the sensor tag 101, which can be used to charge a rechargeable battery in the sensor tag 101. The interface port 140 preferably incorporates an industry-standard interface, such as Ethernet, serial port, or USB, and in the case of USB, interface port 140 may be implemented as, for instance, a micro-USB port or USB Type-C port. The other device connected to the sensor tag 101 via the interface port 140 may include a computer, a storage device, a power source, or any other device capable of interfacing with the sensor tag 101, including the receiver device 102. Where the interface port 140 is used for data connectivity, the interface port 140 preferably allows for two-way data communication between the sensor tag 101 and the other device. Data transmitted from the sensor tag 101 may include, for instance, stored sensor data that is transferred to the other device, device status information, or location data. Data received by the sensor tag 101 may include, for instance, software or firmware updates, or configuration or control settings, or commands.

The audio input/output section 150 provides audio input and output to a user, and may include a speaker and/or microphone. As an output, the audio input/output section 150 emits auditory signals such as tones, alarms, voice messages (e.g., pre-stored audio recordings), and/or other audio signals.

The wireless antenna 160 transmits and/or receives wireless signals. These signals allow for one-way or two-way wireless data communications between the sensor tag 101 and the receiver device 102. The wireless communications may be selected from among a variety of formats, including, but not limited to, WiFi, Bluetooth, Near-Field Communications (NFC), and/or proprietary formats. The transferred data may include some or all of the data described above with respect to the interface port 140.

The attachment component 170 facilitates attachment of the sensor tag 101 to an individual. The attachment component 170 may take the form of a clip, loop, lanyard, chain, etc., or a hook-and-loop type (e.g., Velcro®) fastener. It will be appreciated that the attachment component 170 may be implemented in any other manner where the sensor tag 101 is retained on the user's body.

It will be appreciated that the user interface inputs and outputs described herein are merely examples, and the sensor tag 101 may include other forms and modes of user interface inputs and outputs that are within the scope of the invention.

Figure 2B:
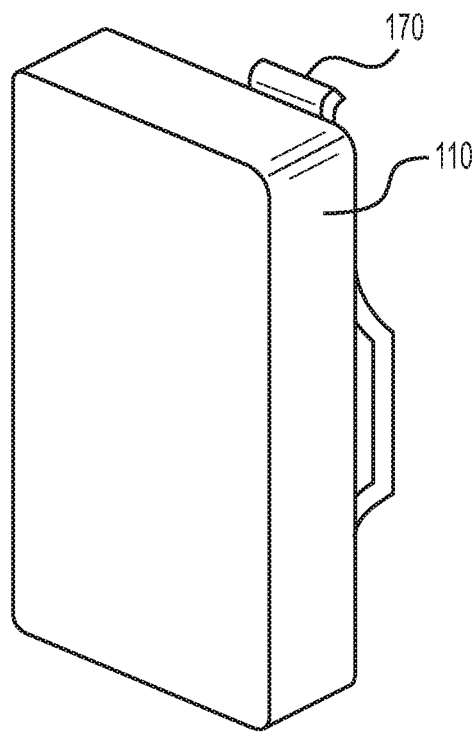
FIG. 2b illustrates another sensor tag in accordance with another embodiment of the invention.

Additionally, it will further be appreciated that the sensor tag 101 may include only a subset of the above-described features. That is, some of the above-described features may be optional in the sensor tag 101. For instance, the visual input section 120, user input section 130, and/or audio input/output section 150 may be optional, and thus potentially omitted from the sensor tag 101. As another example, as illustrated in FIG. 2b, the sensor tag 101 may be implemented solely with the housing 110 and internal components, omitting a user interface and/or even the interface port 140. It will be appreciated that under this implementation, the sensor tag 101 preferably includes the wireless antenna 160 and/or wireless (e.g., induction) charging capabilities, allowing the use of a sealed housing 110 for improved resistance to environmental elements (e.g., water) and durability.

Figure 2C:
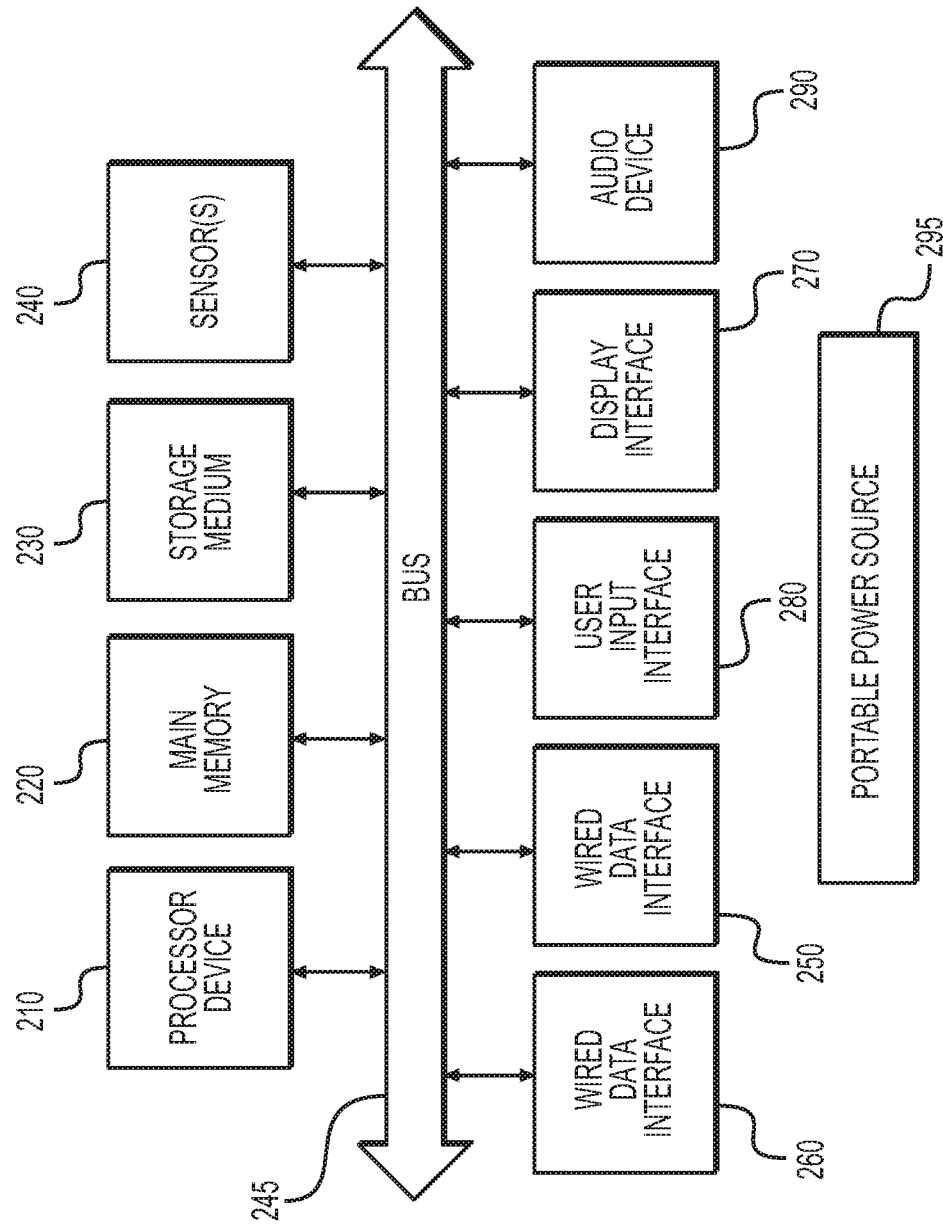
FIG. 2c is a schematic diagram of a sensor tag in accordance with an embodiment of the invention.

FIG. 2c illustrates the internal components contained within the sensor tag 101. The sensor tag 101 includes at least one processor 210, a main memory 220, a storage medium 230, one or more sensors 240, a wired data interface 250, a wireless data interface 260, a display interface 270, a user input interface 280, an audio interface 290. The sensor tag 101 also includes a data bus 245 interconnecting these components and used to transfer data between the components. The sensor tag 101 further includes a portable power source 295.

The processor 210 that controls the various functions of the sensor tag 101. It will be appreciated that the processor 210 may be implemented as a single processor or as a set of multiple processors. The main memory 220 stores, among other things, instructions and/or data for execution by the processor. The main memory may include banks of dynamic random access memory (DRAM), as well as cache memory. It is appreciated that in one embodiment, one or more components of the sensor tag may be implemented as an Application Specific Integrated Circuit (ASIC).

The sensor tag 101 further includes a storage medium 230, a wired data interface 250, a wireless data interface 260, a display interface 270, a user input interface 280, and an audio interface 290. The sensor tag 101 may additionally include a portable power source 295 (e.g., rechargeable lithium ion battery) for powering the device.

The storage medium 230 stores an operating program to be executed by the processor 210, along with other data including, for instance, measurement data collected from the sensor(s) 240. The storage medium 230 may incorporate one or more memory types (e.g., flash memory) and/or may include a removable memory card (e.g., SD, micro-SD).

The wired data interface 250 is coupled to the interface port 140 and the processor 210. The wired data interface 250 controls the interface port 140 to provide data communication between the processor 210 and an external device attached to the interface port 140, such as the receiver device 102.

The wireless data interface 260 is coupled to the wireless antenna 160 and the processor 210. The wireless data interface 260 controls the wireless antenna 160 to provide data communication between the processor 210 and a remote wireless device, such as the receiver device 102.

The display interface 270 is coupled to the visual output component 120 and the processor 210. The display interface 270 controls the operation of the graphical display 120*a* and/or light indicators 120*b*, as applicable, so as to display a desired visual output as instructed by the processor 210. The display interface 270 includes a graphics subsystem that receives textual and graphical information, and processes the information for output to one or more visual output components 120.

The user input interface 280 is coupled to the user input section 130 and the processor 210. The user input interface 280 provides a corresponding signal to the processor 210 when a user input section 130 is manipulated by a user.

The audio interface 190 is coupled to the audio input/output section 150 and the processor 210. The audio interface 280 receives audio input from an input portion of the audio input/output section 150 (e.g., microphone) and provides the input information to the processor 210. The audio interface 280 also provides audio output information to an output portion of the audio input/output section 150 (e.g., speaker) to emit as sound.

The sensor device further includes one or more sensors 240, such as a mechanical sensor. The mechanical sensor may be an accelerometer or another type of sensor configurable to measure acceleration. In addition, the sensor may measure other conditions instead of, or in addition to, acceleration.

For explanatory purposes, all components in the sensor tag are shown as being coupled to, and intercommunicating via, the bus 245. However, the sensor tag is not so limited. Components of the sensor tag may be coupled via one or more data transport means. For example, the processor 210 and/or the main memory 220 may be coupled via a local microprocessor bus. The various components of the sensor tag may be may be coupled via one or more input/output (I/O) buses. The storage medium 230 may be a nonvolatile storage device for storing data and/or instructions for use by the processor 210. In a software embodiment, the storage medium 230 is configured for loading its contents into the main memory 220.

Each computing-related component of the sensor tag may represent a broad category of a computer component of a general and/or special purpose computer. Components of the sensor tag are not limited to the specific implementations provided here.

Figure 2D:
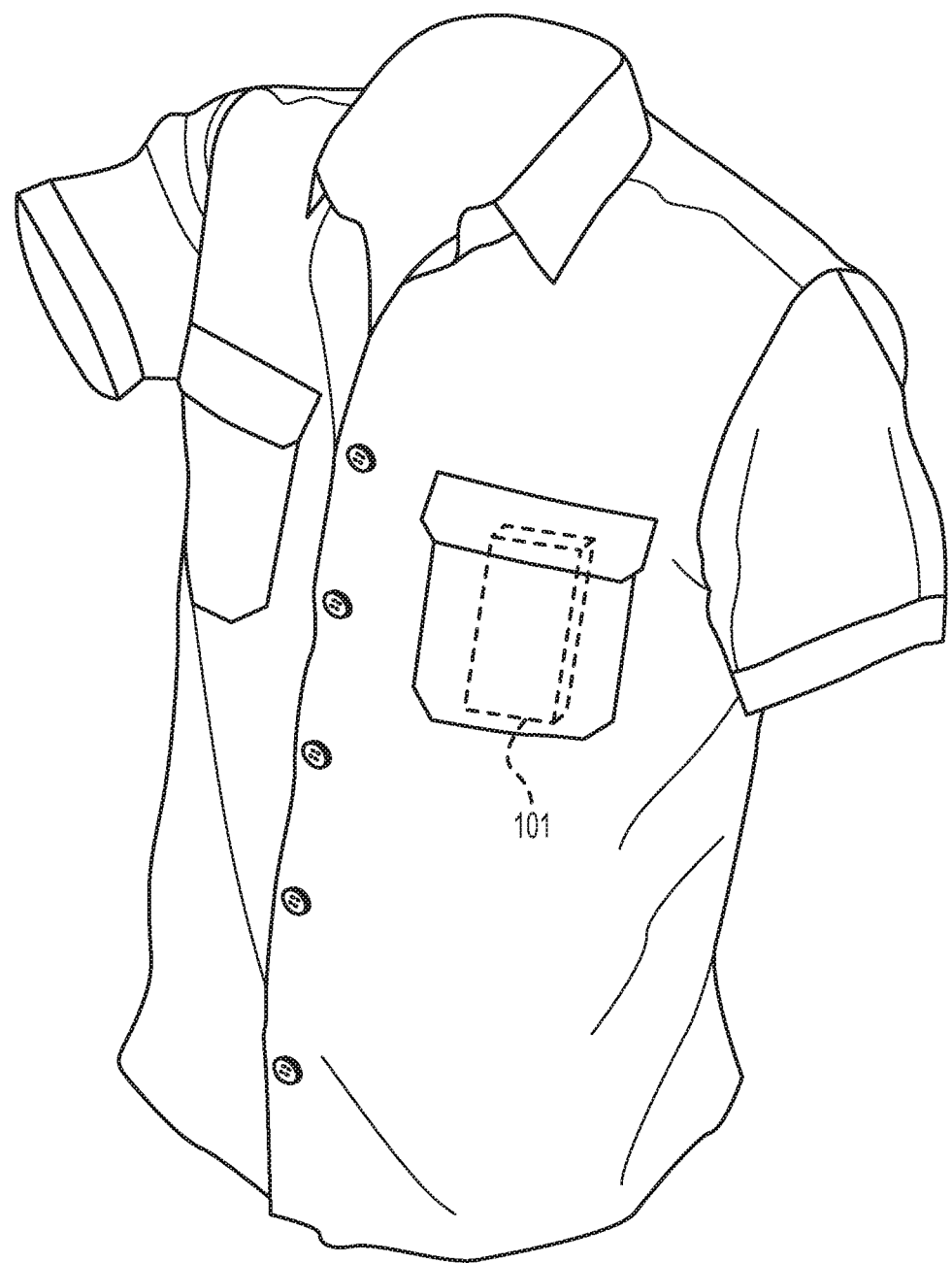
FIG. 2d illustrates an example for placing a sensor tag on an individual.

FIG. 2*d* illustrates an example of how the sensor tag 101 may be placed on an individual. As shown in this example, an individual's clothing includes a pocket, and the sensor tag 101 is inserted into the pocket. A flap, zipper, or other retention mechanism is used to ensure that the sensor tag 101 does not inadvertently fall out of the pocket. It will be appreciated that the positioning of the pocket in this illustration is merely exemplary, and that the pocket may be positioned in any area of clothing or in an existing pocket of the individual's shirt, jacket, pants, etc. It will also be appreciated that the sensor tag 101 may be attached to the individual through other means, such as using the attachment component 170.

Figure 3:
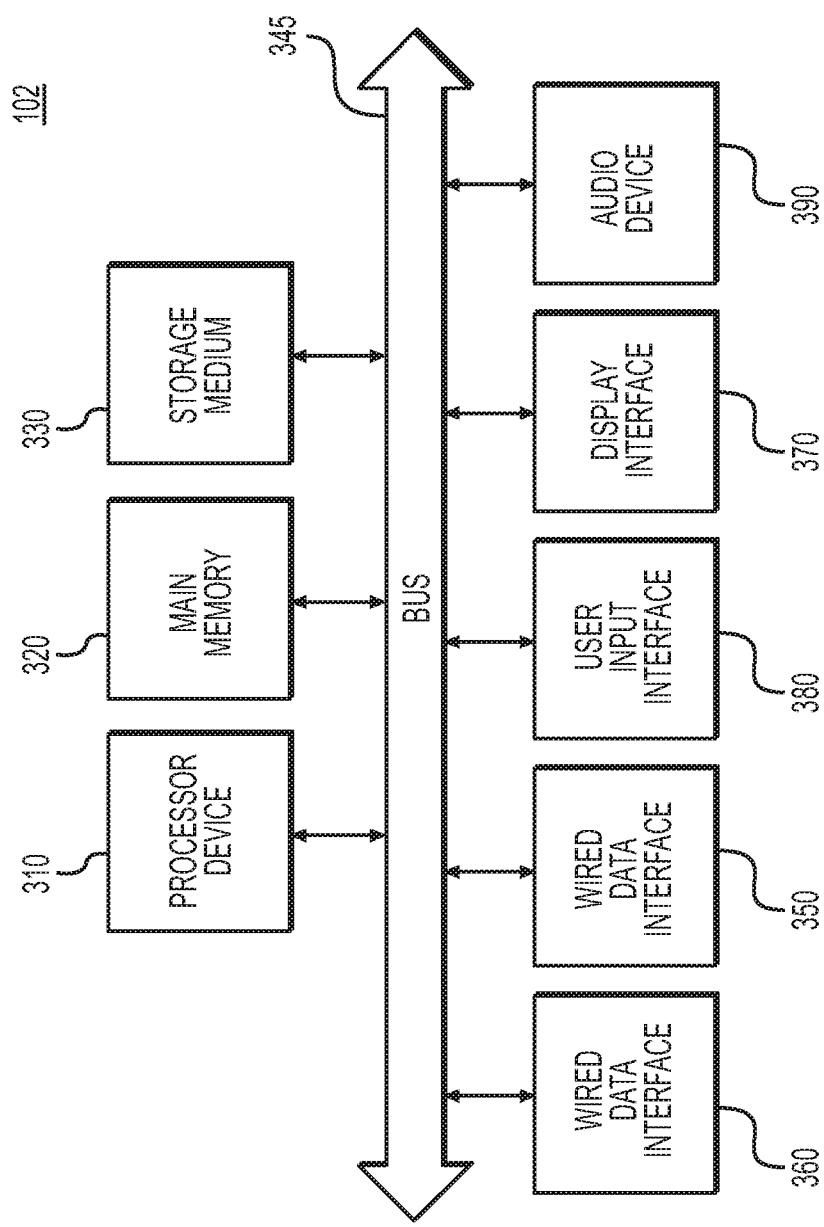
FIG. 3 is a schematic diagram of a receiver in accordance with an embodiment of the invention.

FIG. 3 illustrates the receiver device 102 in accordance with an embodiment of the invention. The receiver device 102 includes one or more processors 310, a main memory 320, and an interconnect bus 345. The processor 310 may include, without limitation, a single microprocessor, or may include a plurality of microprocessors for configuring the receiver device as a multi-processor system. The main memory 320 stores, among other things, instructions and/or data for execution by the processor 310. The main memory 320 may include banks of dynamic random access memory (DRAM), as well as cache memory. It is appreciated that in one embodiment, one or more components of the receiver device 102 may be implemented as an Application Specific Integrated Circuit (ASIC).

The receiver device 102 further includes a storage medium 330, a wired data interface 350 (e.g., USB and/or Ethernet), a wireless data interface 360 (e.g., WiFi, Bluetooth, and/or NFC), a display interface 370 to control display components of the receiver device 102 (e.g., visual indicators, LEDs, and/or graphical display), a user input interface 380 that receives data from user input features of the receiver device 102 (e.g., physical buttons, switches, keyboard, mouse and/or touchscreen), and an audio interface 390 that controls audio components of the receiver device 102 (e.g., speaker and/or microphone). For explanatory purposes, all components in the receiver device 102 are shown in FIG. 3 as being coupled via the bus 345. However, the receiver device 102 is not so limited. Components of the receiver device 102 may be coupled via one or more data transport means. For example, the processor 310 and/or the main memory 320 may be coupled via a local microprocessor bus. Any or all of the components may be coupled via one or more input/output (I/O) buses. The storage medium 330 may be a nonvolatile storage device for storing data and/or instructions for use by the processor 310, and may be implemented, for example, with a magnetic disk drive, an optical disk drive, solid-state disk drive, RAID architecture, network-attached storage, or distributed cloud storage. In a software embodiment, the storage medium 330 is configured for loading its contents into the main memory 320. The wired data interface 350 may be used to communicate across a wired connection (e.g., USB) with the wired data interface 250 of a sensor tag 101.

The user input interface 380 provides interaction with a user of the receiver device. The user input interface 380 may include a keypad and/or a cursor control device. The keypad may be configured for inputting alphanumeric characters and/or other key information. The cursor control device may include, for example, a handheld controller or mouse, a trackball, a stylus, and/or cursor direction keys. In order to display textual and graphical information, the receiver device may include a display interface that may include a graphics subsystem and/or an output display. The output display connected to the display interface 370 may include one or more displays such as a CSTN (Color Super Twisted Nematic), TFT (Thin Film Transistor), TFD (Thin Film Diode), OLED (Organic Light-Emitting Diode), AMOLED display (Activematrix organic light-emitting diode), electronic paper (e.g., e-book), and/or any other type of graphical display. The displays can also be touchscreen displays, such as capacitive and resistive-type touchscreen displays. The display interface 370 includes a graphics subsystem that receives textual and graphical information, and processes the information for output to the output display.

Each component of the receiver device may represent a broad category of a computer component of a general and/or special purpose computer. Components of the receiver device are not limited to the specific implementations provided here.

Accelerometer as Sensor

In one embodiment of the invention, at least one of the sensors 240 of the sensor tag 101 is implemented as an accelerometer. An accelerometer provides measurement of a property known as "proper acceleration" (or "g-force"). Proper acceleration is based on relativity theory, and is a measurement of the physical acceleration experienced by an object relative to a free-fall observer (also known as an inertial observer) momentarily at rest relative to the object. It should be recognized that proper acceleration differs from "coordinate acceleration" (i.e., the rate of change of velocity), as coordinate acceleration is dependent on a particular coordinate system and therefore upon a choice of observers.

A free-falling object (e.g., falling towards the center of the Earth at a rate of approximately 9.81 m/s$^2$) has a proper acceleration of zero, while an object resting on the Earth's surface has a proper acceleration of 9.81 m/s$^2$ in the direction away from the Earth center. In other words, gravitational force does not contribute to proper acceleration, as the inertial observer (against which the proper acceleration is measured) is likewise subject to gravitational force. Notably, inertial observers have a proper acceleration of zero.

Figure 4:
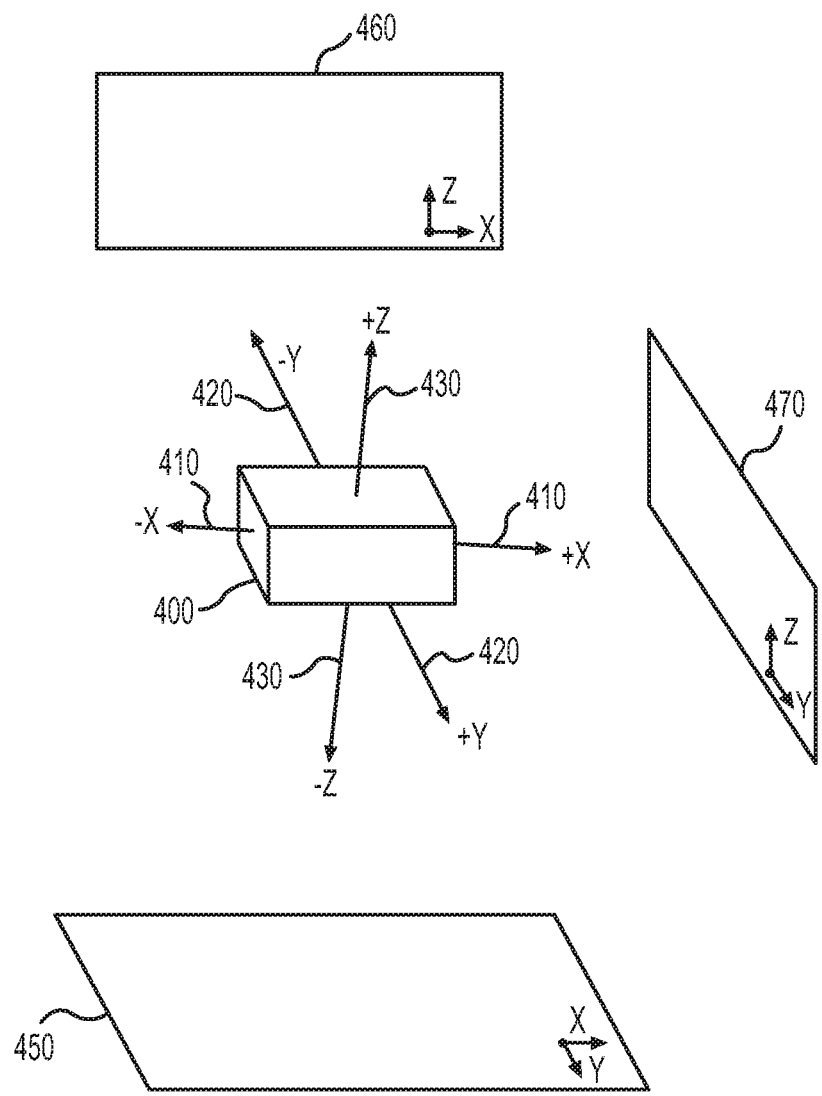
FIG. 4 illustrates an accelerometer used in an embodiment of the invention.

FIG. 4 illustrates an example of an accelerometer 400 that may be incorporated as one or more of the sensors 240. The accelerometer 400 measures proper acceleration along three different directions (e.g., +/−X direction 410, +/−Y direction 420, and +/−Z direction 430) in a three-dimensional (3-D) space. In one embodiment of the invention, each of the three proper acceleration measurement directions is orthogonal to the other two directions, but it will be appreciated that other embodiments of the invention includes accelerometers which measure proper acceleration in directions that are not necessarily orthogonal, and/or in a number of directions other than three.

Projection of Proper Acceleration onto 2-D Planes

In one embodiment of the invention, proper acceleration measurements from the accelerometer 400 for the three directions (e.g., X, Y, and Z) are projected (e.g., plotted) onto three two-dimensional (2-D), non-parallel planes. In the simplest form, the non-parallel planes (e.g., X-Y plane 450, X-Z plane 460, and Y-Z plane 470) are defined according to each two of the three directions. That is, the X-Y plane 450 represents the magnitude and direction of proper acceleration in the X and Y directions, and the X-Z plane 460 and Y-Z plane 470 similarly represent the magnitude and direction of proper acceleration in each of their respective two directions. Of course, it will be appreciated that the planes can be defined according to directions other than the X, Y, Z directions, and that a quantity of 2-D planes may be different than three. These projections produce proper acceleration vectors in each of the 2-D planes.

In one aspect of the invention, the processor 210 within the sensor tag 101 performs the projections of the acceleration data onto the 2-D planes. In another aspect of the invention, the projection is performed by a separate device, such as the processor 310 of the receiver device 102. In the latter case, the sensor tag 101 may intermittently, or continuously (e.g., in real-time), transmit the acceleration measurement data to the receiver device 102 without having undergone some or all of the projection process.

The accelerometer 400 is configured to collect multiple sets of measurements at different timings. These timings may be based on a periodic time interval, which may be predetermined in advance, or on-demand upon request from the from the processor 210. After collecting multiple sets of measurement data, the data is collectively projected (e.g., plotted) onto the same three 2-D planes 450, 460, and 470. This process produces plots of proper acceleration along each 2-D plane, such as the plots illustrated in FIGS. 5(a)-(c). In these plots, both axes represent acceleration (m/s$^2$) in the corresponding direction.

In one embodiment of the invention, data sets are stored and processed within a moving time window. The moving time window may be established as, for instance, a particular number of sensor measurement samples or time intervals, or a particular period of time. Measurement data within the moving time window is maintained and analyzed, and when new measurement data is generated at the next time interval, the oldest measurement within the moving time window is discarded. As such, the moving time window continuously updates ("moves") to reflect the present time, looking backwards for a certain period, and the proper acceleration data. For the plots illustrated in FIGS. 5(a)-(c), the plotted data is based on a certain quantity of collected proper acceleration data samples that corresponds to a particular time window.

In one embodiment of the invention, when the sensor tag 101 is worn by an individual, the system 100 determines, by analyzing proper acceleration data within the moving time window, whether movements of the individual are proper or not. For instance, the system 100 determines whether the individual is properly bending at the knees, as opposed to improperly bending his/her back. The inventors have discovered that, when analyzing a bend as a body movement, a correct bend (e.g., at the knee) is reflected by the majority of the acceleration being toward and away from the ground, while an incorrect bend (e.g., at the waist) is reflected by a considerable amount of motion parallel to the ground as well.

Figure 5A:
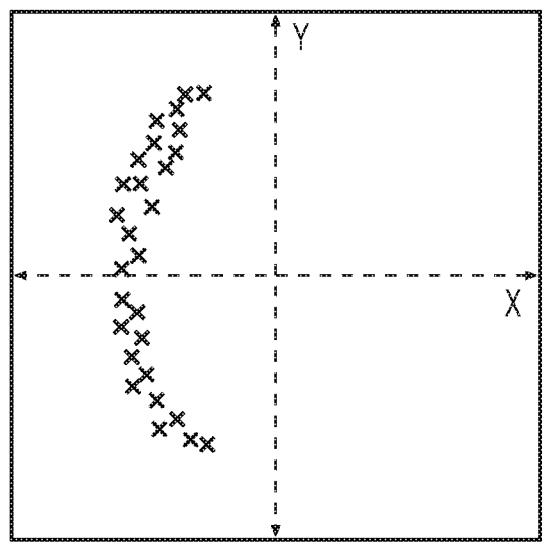
FIGS. 5(a)-(c) are plots of proper acceleration projected onto three 2-D planes.
Figure 5B:
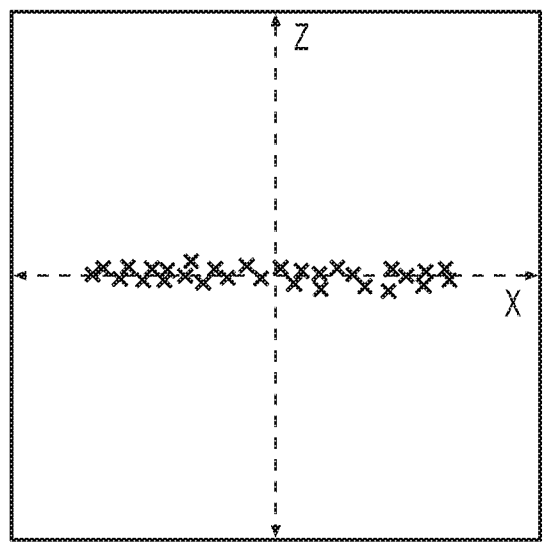
Figure 5C:
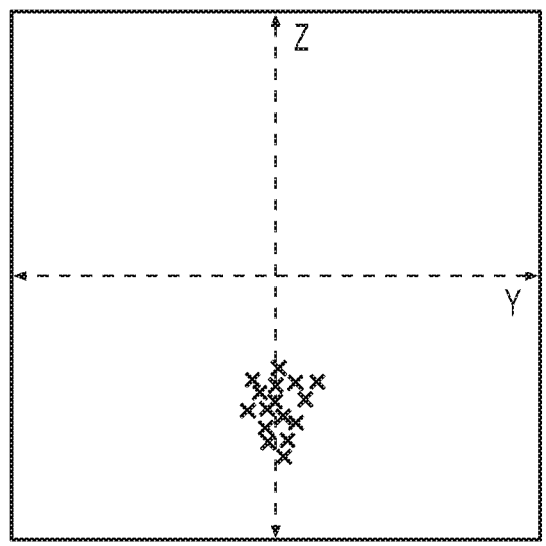
Figure 6A:
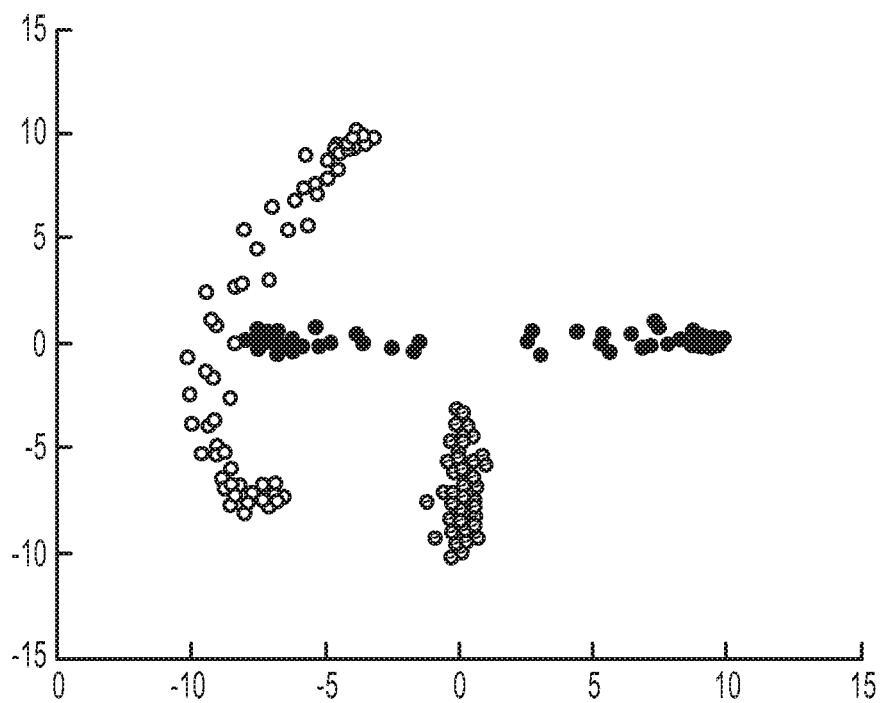
FIGS. 6(a)-(b) are overlay plots of projected proper acceleration from three 2-D planes, where FIG. 6(a) corresponds to an improper bend and FIG. 6(b) corresponds to a proper bend.
Figure 6B:
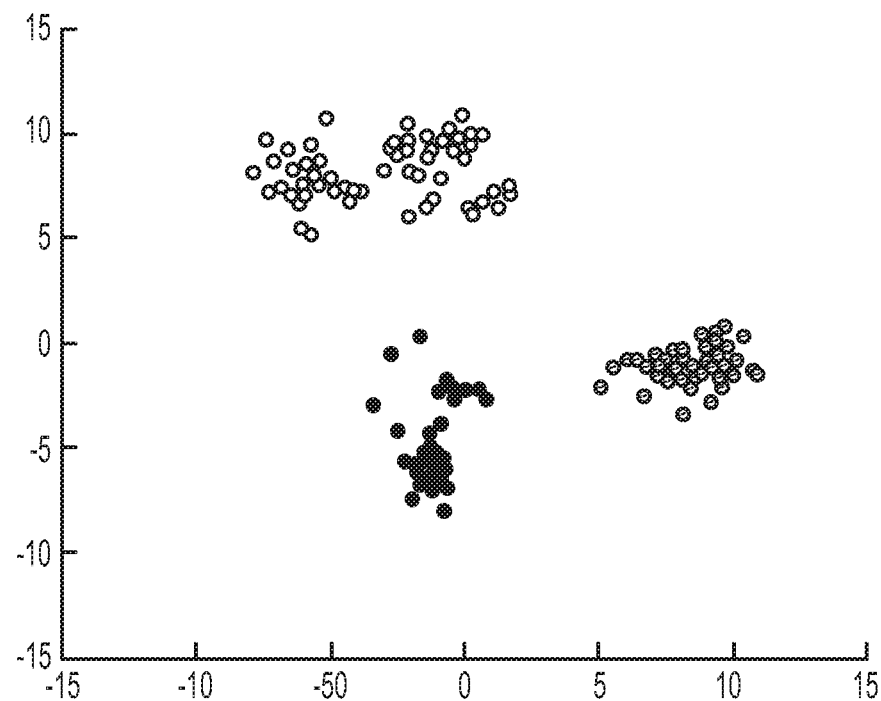

FIG. 6(a) depicts the plots from FIGS. 5(a)-(c) across the three planes 450, 460, and 470, overlaid together onto a single plot. Based on experiments performed by the inventors, FIG. 6(a) represents an example of proper acceleration data that is collected when a subject performs an improper bend (e.g., bending at the waist). On the other hand, based on the inventors' experiments, FIG. 6(b) represents an example of proper acceleration data that is collected when a subject performs a correct and proper bend (e.g., bending at the knees). From a visual perspective, the accelerations projected on the three 2-D planes are more bunched up when the body movement (e.g., bend) is correct and more smeared long when the body movement is incorrect. That is, the difference between the acceleration reported parallel to the ground and perpendicular to the ground causes at least one of these projections to show a swing from positive to negative accelerations if the bend is incorrect and no such swings when the bend is correct.

It will be appreciated that when the number of measured acceleration directions is different than three (e.g., greater than three), the 2-D planes may be based on every combination of two directions, or alternatively, may be a subset of all such combinations. For instance, in the case of four measured acceleration directions, there are six possible 2-D planes (i.e., 3+2+1=6) based on every combination of two directions, and the system may select either all six 2-D planes or a portion of those 2-D planes (e.g., only three of the six possible 2-D planes), onto which the acceleration data is projected.

Calculation of Phasor Angles

Although the plots between FIG. 6(a) and FIG. 6(b) are visually distinguishable, a problem still remains as to establishing an analytical methodology to accurately and efficiently provide a distinction between proper and improper cases. One particularly effective approach discovered by the inventors is to calculate a phasor angle for each acceleration sample point in time, and use the calculated phasor angles to distinguish between proper movement (e.g., correct bend) and improper movement (e.g., incorrect bend), as described in greater detail below. The inventors have found that this approach has the particular benefits of being easily scalable and straightforward to implement, requiring relatively few number of calculations, and producing minimal errors in estimates caused by small user motions.

The calculation of phasor angles, according to one embodiment of the invention, will now be described. For each acceleration measurement sample, the phasor angle for the measurement sample along each of the three 2-D planes is calculated. The phasor angle for each 2-D plane is calculated as the inverse tangent of the ratio of the two accelerations along the dimensions defining the 2-D plane. For example, for a measurement sample, the phasor angle $\theta_{XY}$ along the X-Y plane 450 is calculated as:

$$\theta_{XY} = \tan^{-1} \frac{\text{(acceleration magnitude along the } X \text{ direction)}}{\text{(acceleration magnitude along the } Y \text{ direction)}}$$

Similarly, phasor angles $\theta_{XZ}$ and $\theta_{YZ}$ along the X-Z plane 460 and Y-Z plane 470, respectively, are calculated for the measurement sample.

As an alternative to the inverse tangent operation, the phasor angle may be determined by accessing a look-up table. In an embodiment where the phasor angle is calculated within the sensor tag 101, the look-up table may be stored in the storage medium 230, and loaded into the main memory 220. In an embodiment where the phasor angle is calculated within the receiver device 102, the look-up table may be stored in the storage medium 330 and loaded into the main memory 320. The use of a look-up table improves the speed of operation by minimizing the required mathematical calculations. It will be appreciated that other approaches may be used to determine the phasor angle.

In an embodiment of the invention, a filter is applied to acceleration vectors, so as to discard acceleration vectors having a magnitude smaller than a threshold TH1 (e.g., corresponding to minimal movement). The inventors have discovered that a threshold of 9 m/s² provides good results. However, it will be appreciated that the threshold TH1 may be set to a different value.

In one aspect of the invention, the processor 210 within the sensor tag 101 performs the filtering and calculations of the phasor angles. In another aspect of the invention, the filtering and/or calculations are performed by a separate device, such as the processor 310 of the receiver device 102. In the latter case, the sensor tag 101 may intermittently, or continuously (e.g., in real-time), transmit the acceleration measurement data to the receiver device 102 without having undergone some or all of the filtering and/or phasor angle calculations.

Use of Phasor Angles to Determine Proper vs. Improper Body Movements

According to one embodiment of the invention, the calculated phasor angles are analyzed to determine whether or not an individual's body movement is proper. This process will now be described. Initially, the phasor angles are calculated for all collected measurement samples over the moving time window. Next, for each 2-D plane, the largest and the smallest calculated phasor angle within the moving time window is determined. For instance, for the X-Y plane 450, among the phasor angles $\theta_{XY}$ for the acceleration samples within the moving time window, the largest of the phasor angles $\theta_{XY\text{-}max}$ and the smallest of the phasor angle $\theta_{XY\text{-}min}$ is determined. Then, the absolute value difference $\Delta\theta_{XY}$ between the largest and the smallest phasor angle, for the X-Y plane 450, within the moving time window is calculated (i.e., $\Delta\theta_{XY}=|(\theta_{XY\text{-}max})-(\theta_{XY\text{-}min})|$). These steps are repeated for the remaining 2-D planes, such that, within an instance of the moving time window, the difference $\Delta\theta$ between the largest and the smallest phasor angle for each 2-D plane (e.g., $\Delta\theta_{XY}$, $\Delta\theta_{XZ}$, and $\Delta\theta_{YZ}$) is calculated.

Next, it is determined whether any of the differences $\Delta\theta$ exceeds a threshold value TH2. If any one of the differences $\Delta\theta$ exceeds threshold TH2, it is determined that the body movement occurring within the moving time window is improper (e.g., improper bend). On the other hand, if this difference does not exceed the threshold value, it is determined that the body movement occurring within the moving time window is proper. That is, if any one of $\Delta\theta_{XY}$, $\Delta\theta_{XZ}$, and $\Delta\theta_{YZ}$ exceeds TH2, it is determined that an improper body movement has occurred within the moving time window.

For the threshold TH2, the inventors have discovered that values of 90° and 100° (and values therebetween) are thresholds providing good results. A 90° angle difference threshold also makes sense logically, since such an angle difference reflects a swing of acceleration from one quadrant within the 2-D plane to another quadrant, thereby indicating that at least one of the accelerations has made a wide swing, as is illustrated in FIG. 6(a). Of course, it will be appreciated that other threshold values may be used within the scope of the invention, and that depending on the circumstances, different thresholds may even be compared against phasor angles of different 2-D planes.

Figure 7A:
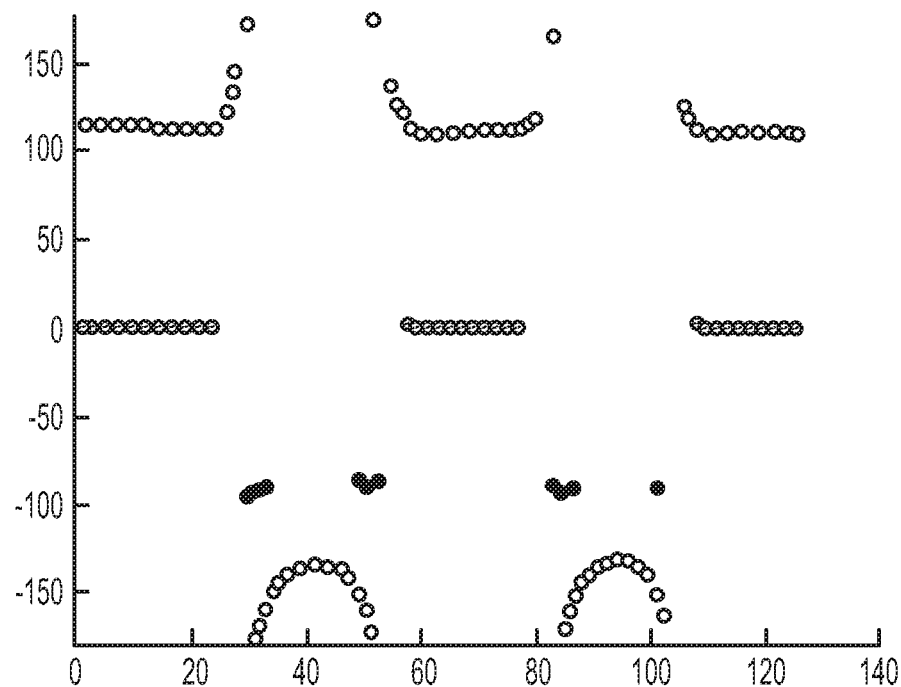
FIGS. 7(a)-(b) are plots of proper acceleration phasor angles with respect to time, where FIG. 7(a) corresponds to an improper bend and FIG. 7(b) corresponds to a proper bend.
Figure 7B:
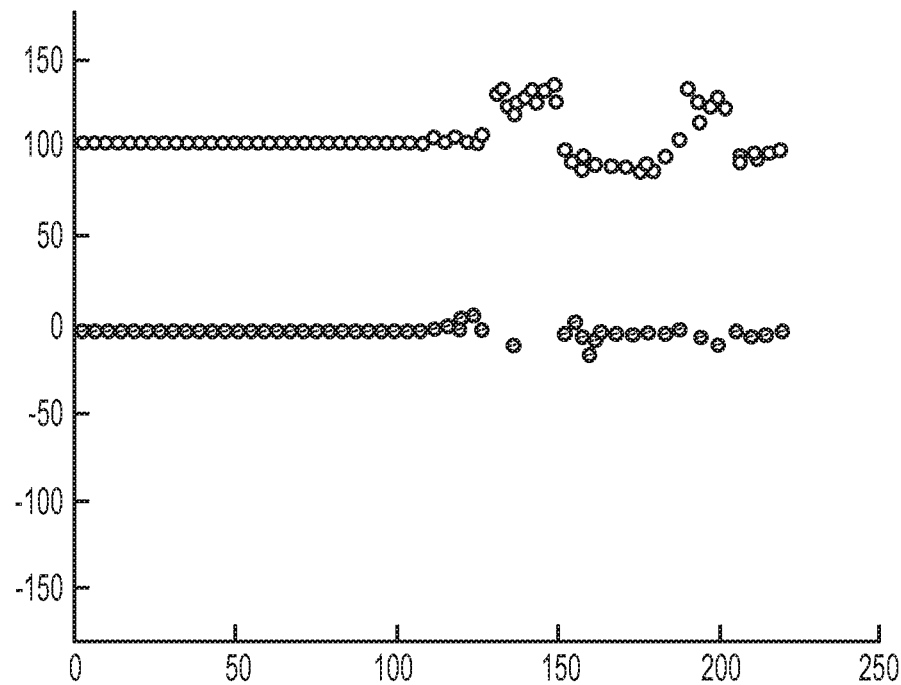

FIGS. 7(a) and (b) illustrate the phasor angles for the 2-D planes over a period of time, with FIG. 7(a) being an example of an incorrect body motion (e.g., incorrect bend) and FIG. 7(b) being an example of a correct body motion (e.g., correct bend). In FIGS. 7(a) and (b), the horizontal axes represents the sample time, while the vertical axes represent the calculated phasor angles. As shown in FIG. 7(a), the swing in phasor angles for one of the 2-D planes exceeds 90° within the shown set of data samples, and therefore, it is determined that an improper body movement has occurred. On the other hand, in FIG. 7(b), the swings in phasor angles for all three 2-D planes does not exceed 90°, and therefore, it is determined that no improper body movement has occurred. It is noted that in one embodiment, even a single instance where the phasor angle spread exceeds the threshold is sufficient to be classified as an improper body movement. This approach is particularly adaptable to detecting improper back bends. Nonetheless, in another embodiment, the phasor angle spread must exceed the threshold for a predetermined period (e.g., number of measurement samples or amount of time) in order to be classified as an improper body movement. And in yet another embodiment, the phasor angle spread must exceed the threshold a certain number of times within a certain period, in order to be classified as an improper body movement.

It will be appreciated that the moving time window size can be set to a static (e.g., predetermined) value or can be dynamically adjusted, but regardless, should preferably correspond to an appropriate amount of time sufficiently long to capture one whole improper body movement (e.g., bend), even if such movement is performed relatively slowly. In addition, the interval between acceleration measurement samples should likewise be set to an appropriate level that is sufficient to capture the swings in phasor angles so as to recognize an improper body movement. In one embodiment, the moving time window is set as 20 measurement samples or about 2 seconds.

It is recognized that incorporating a moving time window reduces the effect of old movements from having an undue effect on estimation of new movements. Also, in the case that the sensor tag 101 continuously transmits measurement sample data using a wireless access scheme, one or more measurement samples received in error could cause the algorithm to provide erroneous estimates, but using a moving time window minimizes such from propagating forward.

Figure 8A:
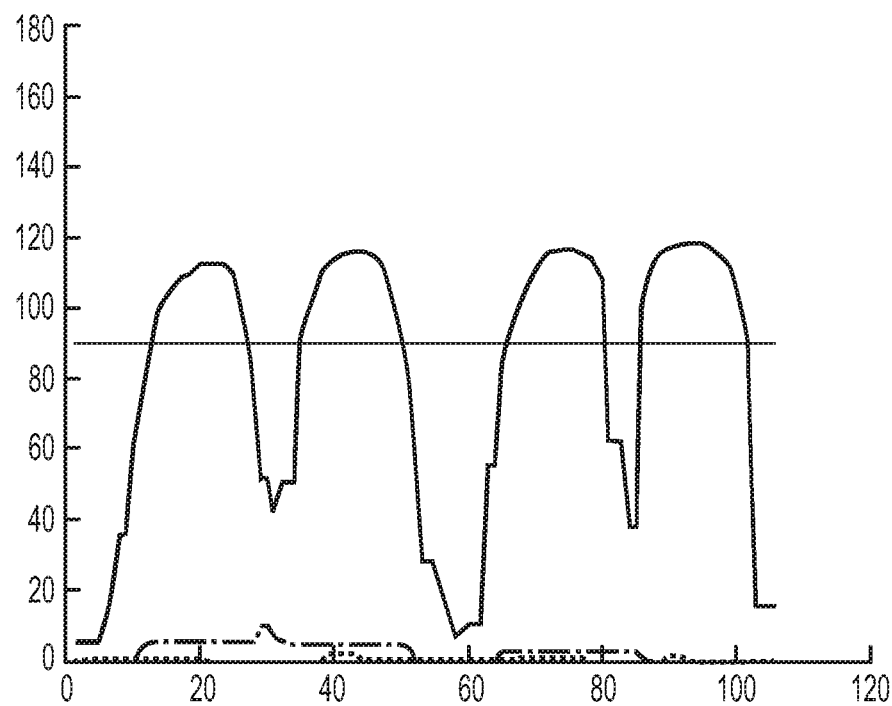
FIGS. 8(a)-(b) are plots of the spread in proper acceleration phasor angles with respect to time for a moving time window, where FIG. 8(a) corresponds to an improper bend and FIG. 8(b) corresponds to a proper bend.
Figure 8B:
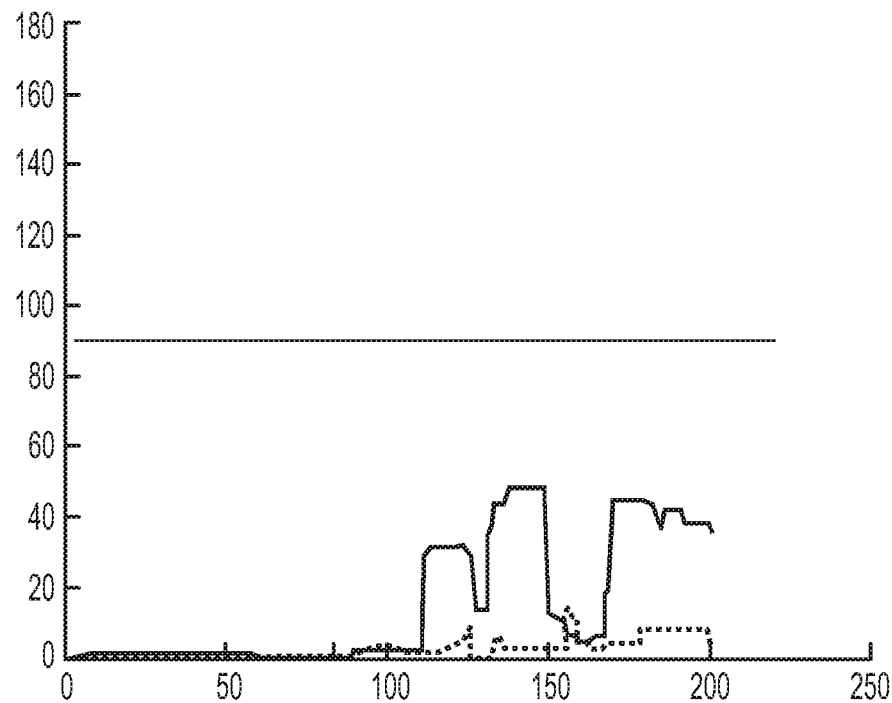

Moreover, it will be appreciated that the phasor angle differences Δθ may be analyzed as a time-varying characteristic, with the moving time window continuously updating. This analysis is illustrated in FIGS. 8(*a*) and (*b*), where the horizontal axis represents a time of a moving time window, and the vertical axis represents the phasor angle difference for each 2-D plane. FIG. 8(*a*) illustrates an example for an incorrect body movement (e.g., bend), as the phasor angle differences for one of the 2-D planes exceeds threshold TH2 (set at 90° in the example of FIGS. 8(*a*) and (*b*)) at several instances. On the other hand, FIG. 8(*b*) illustrates an example for a correct body movement, where phasor angle differences for all three 2-D planes never exceeds the 90° threshold. Using this monitoring approach, the system 100 continuously analyzes updated moving time windows with each new measurement sample.

In one aspect of the invention, the processor 210 within the sensor tag 101 performs the described analysis of the moving time window for phasor angles exceeding the threshold. In another aspect of the invention, this process is performed by a separate device, such as the processor 310 of the receiver device 102. In the latter case, the sensor tag 101 may intermittently, or continuously (e.g., in real-time), transmit the acceleration measurement data to the receiver device 102 without having undergone some or all of the filtering and/or phasor angle calculations.

It will be appreciated that instead of phasor angles, other characteristics of acceleration data may be used to distinguish between proper and improper body movements.

Advantages of Using Accelerometer as Sensor

The inventors have discovered that incorporating an accelerometer to determine improper body movements has notable advantages. In particular, the system 100 observes all three 2-D planes as reported by the accelerometer (with a moving coordinate system), without requiring the correction needed for a space-based fixed coordinate system. As such, the use of proper acceleration measurements allows the sensor tag 101 to operate regardless of the orientation that the sensor tag 101 is attached to a subject. Therefore, regardless of the orientation in which the sensor tag is attached to a subject (even if the subject wears the sensor tag 101 backwards), the sensor tag 101 correctly determines an improper body movement from the proper acceleration measurements. Additionally, if the sensor tag 101 changes position over time (e.g., over the work day), the sensor tag 101 continues to correctly function. Moreover, since the proper acceleration measurements do not depend on a fixed coordinate system, the placement of the accelerometer sensor within the sensor tag 101 does not impact the functioning of the sensor tag 101. Thus, the use of proper acceleration measurements avoids these real-world issues that could arise when analyzing movement based on a fixed coordinate system.

Another benefit to using an accelerometer is that calibration is unnecessary, either during initial production or during operation, to accurately detect improper body movement. Since body movement is determined based on relative magnitudes of proper acceleration along two directions (i.e., to calculate the phasor angle for the corresponding 2-D plane), the accelerometer need only be generally precise between the measured directions, but need not necessarily be accurate in a single direction. Of course, it will be appreciated that performing calibration is still within the scope of the invention, and may still produce incremental improvements in accurately determining body movements.

Yet another benefit to using an accelerometer is that the above-described processing of proper acceleration data is, in general, computationally simplistic, which allows the system 100 to be cost efficient and easily scalable to increased numbers of sensor tags 101.

Operation of the System

Figure 9:
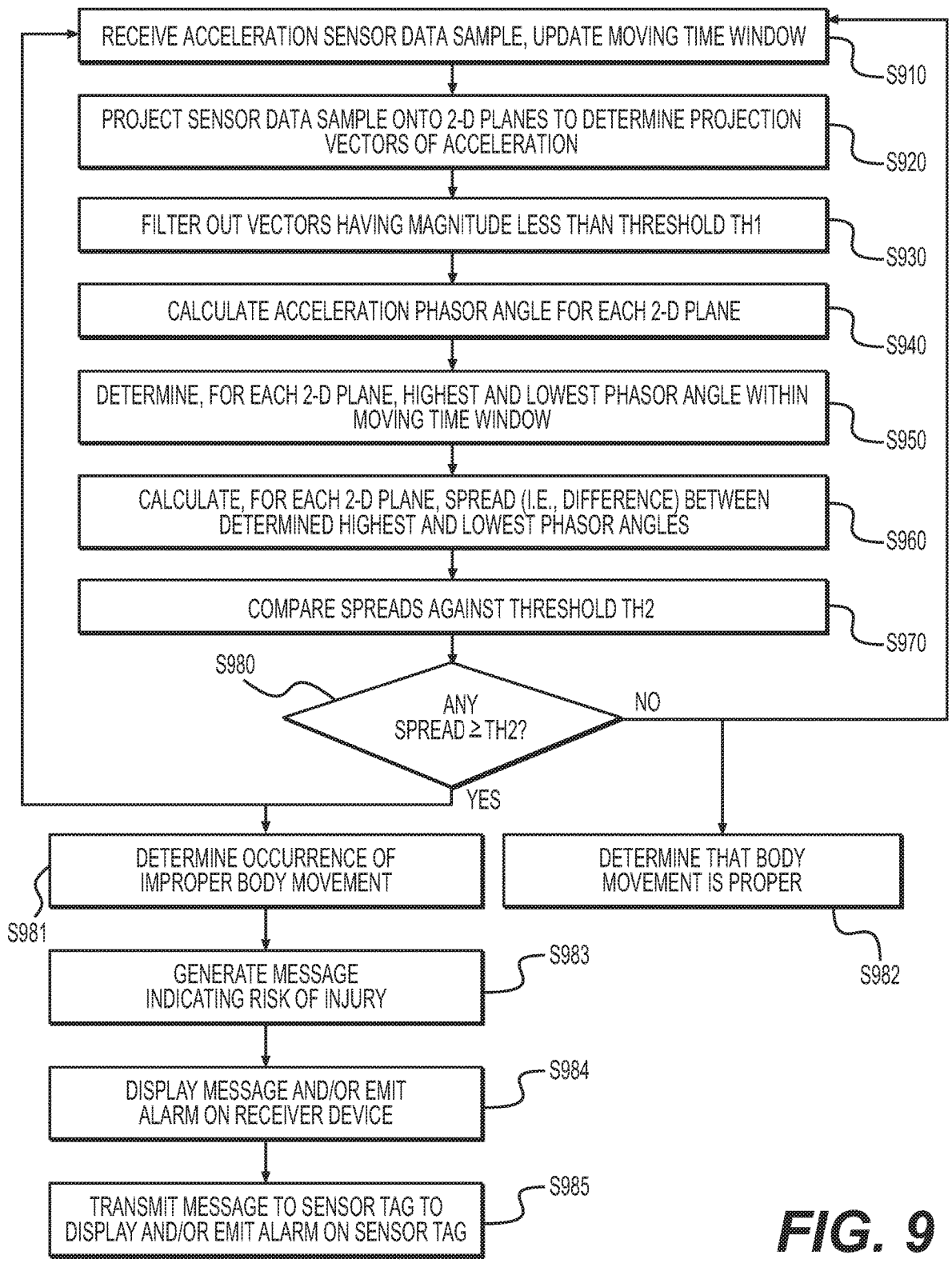
FIG. 9 is a flow chart illustrating the operation of the system in detecting an improper body movement.

FIG. 9 is a flow chart illustrating the operation of the system 100 to determine an improper body movement. In step S910, the processor 310 receives a proper acceleration data sample collected from the acceleration sensor 240 of a sensor tag 101 and transmitted through its wireless interface. The processor 310 updates the moving time window, discarding the oldest data sample within the moving time window.

In step S920, the processor 310 projects the received data sample onto multiple 2-D planes (e.g., X-Y plane 450, X-Z plane 460, Y-Z plane 470) and determines projection vectors of proper acceleration for each 2-D plane. Each projection vector corresponds to a direction and magnitude of proper acceleration in the respective 2-D plane.

In step S930, the processor 310 filters out projection vectors which have a magnitude less than a threshold TH1. This filtering process removes vectors corresponding to small amounts of proper acceleration, which would not constitute major body movements.

In step S940, the processor 310 calculates, for each 2-D plane, an acceleration phasor angle based on the projection vector. This calculation has already been described above (e.g., by using an inverse tangent calculation or by using a look-up table) and will not be repeated. The moving time window is updated to include the calculated phasor angles.

In step S950, the processor 310 determines, for each 2-D plane, the highest and the lowest phasor angle for that 2-D plane within the moving time window. In step S960, the processor 310 calculates, for each 2-D plane, the angle spread (i.e., angle difference) between the highest and the lowest phasor angle for that 2-D plane within the moving time window.

In step S970, the processor 310 compares each of the angle spreads (e.g., three angle spreads for the three 2-D planes) against a threshold TH2. In step S980, the processor 310 determines whether any of the angle spreads equals or exceeds the threshold TH2. If any one of the angle spreads equals or exceeds the threshold TH2, the processor 310 identifies that an improper body movement has occurred within the moving time window, in step S981. Otherwise, the processor 310 identifies that no improper body movement has occurred, in step S982.

If the processor 310 determines, in step S981, that an improper body movement has occurred, the processor 310 generates, in step S983, a message indicating that the corresponding individual is performing a body movement that is potentially subject to (e.g., high risk of) an injury. In step S984, the processor 310 controls the display interface 370 to display the message on a display component of the receiver device 102. In step S985, the processor 310 controls the wireless data interface 360 to transmit the message to the sensor tag 101. When the sensor tag 101 receives the message, the sensor tag 101 may take appropriate steps to notify the corresponding individual, including displaying a visual indication on the visual output section 120 and/or emitting a sound (e.g., alarm or tone) using the audio input/output section 150.

After either determination, the operation awaits the next acceleration data sample, and returns to step S910.

It will be appreciated that each receiver device 102 may interact with one or plurality of sensor tags 101, and may include a dashboard display for a supervisor to monitor the body movements of one or multiple subjects (e.g., workers on an operations floor).

It will also be appreciated that instead of using the processor 310 on the receiver device 102, the steps illustrated in FIG. 9 may be performed instead by the processor 210 on the sensor tag 101. In such instance, steps S984 and S985 may alternatively involve the processor 210 producing the visual notification and/or sound on the sensor tag 101, and transmitting the message to the receiver device 102 to cause a similar visual and/or audio notification on the receiver device 102.

It will be further appreciated that the acceleration data samples, phasor angles, angle spread, or any other information described above may be stored in the respective storage components of the sensor tag 101 (e.g., storage medium 230) and/or the receiver device 102 (e.g., storage medium 330) to be retained for subsequent access and use.

It will additionally be appreciated that steps S984 and S985 are optional steps and may be omitted and/or replaced with other approaches of providing notification.

In another aspect of the invention, the receiver device 102 collects the acceleration samples from each sensor tag 101 at longer intervals (e.g., at the end of each work shift). This collection may be performed wirelessly or with a wired interface (e.g., using the respective wired data interfaces of the sensor tag 101 and the receiver device 102). In such instance, the receiver device 102 may perform the phasor angle analysis across all the collected acceleration samples for the longer interval as a batch process, and provide notification of problematic body movements that occurred in the previous time interval (e.g., previous work shift).

Inventors' Experiments

The inventors have performed experiments using the above-described approach, which revealed that the approach performed perfectly on 7 subjects whose bend approaches were known ahead of time. In a phase of blind testing involving 12 subjects, the inventors' approach scored perfectly in all 12 cases by estimating the correctness of the bends and then checking against a key kept by a test performer.

With the 19 total correct determinations (i.e., 100% score with 19 subjects), the statistical confidence in estimating the accuracy of the inventors' approach is as follows

| 95% Confidence Level | 99% Confidence Level |
| --- | --- |
| Sample Size: 12<br>Population: 100,000,000<br>Percentage: 99%<br>Confidence Interval: 5.63 | Sample Size: 12<br>Population: 100,000,000<br>Percentage: 99%<br>Confidence Interval: 7.41 |

This result shows that if this blind test with 12 subjects (sample size in the table) were to estimate the behavior for a population of 100,000,000 devices (population) and the score was 99% (percentage in the table—note that although the actual score was 100%, the calculator used only accepted scores up to 99%) the system provides a 95% confidence that in real world across all 100,000,000 subjects, the system provides correct determinations between 94.37% (100%-5.63% Confidence Interval) and 100% accuracy. Alternatively, the system provides a 99% confidence that the system will correctly determine improper bends between 92.59% and 100% accuracy.

ALTERNATIVES

It will be appreciated that instead of using phasor angles, other statistical methods, such as variance, skewness and kurtosis, etc. can also be used to distinguish the spread of the collected data.

While the invention has primarily been discussed with respect to back bends, it will be appreciated that the detection of other body movements including, but not limited to, falls due to fainting, slips or trips, etc., is within the scope of the invention.

It will also be appreciated that the sensor tag 101 is not necessarily implemented as a standalone device, but may be incorporated within an existing electronic device such as a smartphone. In particular, since some smartphones may already have built-in accelerometers and wireless data transfer capabilities, the system 100 may be implemented as a software application on an individual's smartphone, relying on the smartphone's existing features.

The embodiments discussed herein are examples of preferred embodiments of the present invention and are provided for illustrative purposes only. They are not intended to limit the scope of the invention. Although specific configurations, structures, materials, etc. have been shown and described, such are not limiting. Modifications and variations are contemplated within the scope of the invention, which is to be limited only by the scope of the issued claims.

Software embodiments of the example embodiments presented herein may be provided as a computer program product, or software, that may include an article of manufacture on a machine-accessible or machine-readable medium having instructions. The instructions on the non-transitory machine-accessible, machine-readable, or computer-readable medium may be used to program a computer system or other electronic device. The machine-accessible, machine-readable, or computer-readable medium may include, but is not limited to, floppy diskettes, optical disks, CDROMs (and writable/rewritable variants thereof), DVDROMs (and writable/rewritable variants thereof), Blu-Rays (and writable/rewritable variants thereof), magneto-optical disks, magnetic disk drives, solid-state (e.g., flash) storage, media or disk drives, portable data storage devices, or other types of media/machine-readable medium suitable for storing or transmitting electronic instructions. The techniques described herein are not limited to any particular software configuration. They may find applicability in any computing or processing environment. The terms "computer-readable", "machine-accessible medium" or "machine-readable medium" used herein shall include any medium that is capable of storing, encoding, or transmitting a sequence of instructions for execution by the machine and that causes the machine to perform any one of the methods described herein. Furthermore, it is common in the art to speak of software, in one form or another (e.g., program, procedure, process, application, module, unit, logic, and so on) as taking an action or causing a result. Such expressions are merely a shorthand way of stating that the execution of the software by a processing system causes the processor to perform an action to produce a result. The user input interface can control the operation and various functions of the receiver device, and can include any components, circuitry, or logic operative to drive the functionality of the receiver device. For example, the user input interface can include one or more processors acting under the control of an application.

What is claimed is:

1. An apparatus for detecting a potential injury condition, comprising:
   a receiver configured to receive sensor data from a sensor worn by an individual, the sensor data containing multi-dimensional acceleration information, along N non-parallel dimensions, corresponding to movement of the individual, wherein N is at least three; and
   a processor configured to determine, based on the sensor data, a potential injury condition of the individual, said processor being configured to:
      project the multi-dimensional acceleration information onto M non-parallel planes thereby generating M projections of acceleration,
      determine a phasor angle of each of the M projections of acceleration for a sample of sensor data taken within a predetermined window of time, and
      determine the potential injury condition based on the determined phasor angles within the predetermined window of time.

2. The apparatus according to claim 1, wherein the predetermined window of time is a moving window, and wherein said processor is further configured to update the M projections of acceleration substantially upon receiving a new sample of sensor data.

3. The apparatus according to claim 1, wherein said processor is further configured to generate potential injury condition data corresponding to the potential injury condition.

4. The apparatus according to claim 1, wherein the acceleration information includes acceleration information sensed along each of N axes at predetermined time intervals.

5. The apparatus according to claim 1, wherein said processor determines the potential injury condition by, for each of the non-parallel planes, comparing an absolute value of a difference between the smallest phasor angle and the largest phasor angle during the predetermined window of time for the respective non-parallel plane with a potential injury condition threshold.

6. The apparatus according to claim 5, wherein said processor is further configured to, in the case that the potential injury condition threshold has been exceeded with respect to any one of the M non-parallel planes, generate a message indicating that the individual is subject to an injury.

7. The apparatus according to claim 5, wherein said processor determines the phasor angle of acceleration in a respective non-parallel plane defined by, out of N sensed axes, a first axis and a second axis, by:
   determining a ratio of the acceleration along the first axis to the acceleration along the second axis, and
   calculating an inverse tangent of the ratio of the acceleration to determine the phasor angle of acceleration.

8. The apparatus according to claim 5, wherein said processor determines the phasor angle of acceleration by accessing a look-up table.

9. The apparatus according to claim 1, wherein the potential injury condition corresponds to exceeding a potential injury condition threshold associated with either a bend of the knees, a bend of the waist, or a combination of both.

10. A method of detecting a potential injury condition, comprising:
    electronically receiving sensor data from a sensor worn by an individual, the sensor data containing multi-dimensional acceleration information, along N non-parallel dimensions, corresponding to movement of the individual, wherein N is at least three; and
    electronically determining, using a processor and based on the sensor data, a potential injury condition of the individual, wherein said processor:
       projects the multi-dimensional acceleration information onto M non-parallel planes thereby generating M projections of acceleration,
       determines a phasor angle of each of the M projections of acceleration for a sample of sensor data taken within a predetermined window of time, and
       determines the potential injury condition based on the determined phasor angles within the predetermined window of time.

11. The method according to claim 10, wherein the predetermined window of time is a moving window, and wherein said determining step further includes updating the M projections of acceleration substantially upon receiving a new sample of sensor data.

12. The method according to claim 10, further comprising:
    generating potential injury condition data corresponding to the potential injury condition.

13. The method according to claim 10, wherein said receiving step includes receiving acceleration information sensed along each of N axes at predetermined time intervals.

14. The method according to claim 10, wherein said determining step determines the potential injury condition by, for each of the non-parallel planes, comparing an absolute value of a difference between the smallest phasor angle and the largest phasor angle during the predetermined window of time for the respective non-parallel plane with a potential injury condition threshold.

15. The method according to claim 14, further comprising:
    generating, in the case that the potential injury condition threshold has been exceeded with respect to any one of the M non-parallel planes, a message indicating that the individual is subject to an injury.

16. The method according to claim 14, wherein said determining step determines the phasor angle of acceleration in a respective non-parallel plane defined by, out of N sensed axes, a first axis and a second axis, by:
    determining a ratio of the acceleration along the first axis to the acceleration along the second axis, and
    calculating an inverse tangent of the ratio of the acceleration to determine the phasor angle of acceleration.

17. The method according to claim 14, wherein said determining step determines the phasor angle of acceleration by accessing a look-up table.

18. The method according to claim 10, wherein the potential injury condition corresponds to exceeding a potential injury condition threshold associated with either a bend of the knees, a bend of the waist, or a combination of both.

19. A non-transitory computer readable storage medium storing one or more programs, the one or more programs comprising instructions, which, when executed by an electronic device with one or more processors, cause the electronic device to perform the steps of:

receiving sensor data from a sensor worn by an individual, the sensor data containing multi-dimensional acceleration information, along N non-parallel dimensions, corresponding to movement of the individual, wherein N is at least three; and determining, based on the sensor data, a potential injury condition of the individual, wherein determining includes:

projecting the multi-dimensional acceleration information onto M non-parallel planes thereby generating M projections of acceleration, determining a phasor angle of each of the M projections of acceleration for a sample of sensor data taken within a predetermined window of time, and determining the potential injury condition based on the determined phasor angles within the predetermined window of time.

20. The computer-readable medium according to claim 19, wherein the predetermined window of time is a moving window, and wherein said determining step further includes updating the M projections of acceleration substantially upon receiving a new sample of sensor data.

21. The computer-readable medium according to claim 19, further comprising:

generating potential injury condition data corresponding to the potential injury condition.

22. The computer-readable medium according to claim 19, wherein said receiving step includes receiving acceleration information sensed along each of N axes at predetermined time intervals.

23. The computer-readable medium according to claim 19, wherein said determining step determines the potential injury condition by, for each of the non-parallel planes, comparing an absolute value of a difference between the smallest phasor angle and the largest phasor angle during the predetermined window of time for the respective non-parallel plane with a potential injury condition threshold.

24. The computer-readable medium according to claim 23, further comprising:

generating, in the case that the potential injury condition threshold has been exceeded with respect to any one of the M non-parallel planes, a message indicating that the individual is subject to an injury.

25. The computer-readable medium according to claim 23, wherein said determining step determines the phasor angle of acceleration in a respective non-parallel plane defined by, of N sensed axes, a first axis and a second axis, by:

determining a ratio of the acceleration along the first axis to the acceleration along the second axis, and calculating an inverse tangent of the ratio of the acceleration to determine the phasor angle of acceleration.

26. The computer-readable medium according to claim 23, wherein said determining step determines the phasor angle of acceleration by accessing a look-up table.

27. The computer-readable medium according to claim 19, wherein the potential injury condition corresponds to exceeding a potential injury condition threshold associated with either a bend of the knees, a bend of the waist, or a combination of both.

28. A system for detecting a potential injury condition, comprising:

a sensor worn by an individual;

a receiver configured to receive sensor data from said sensor, the sensor data containing multi-dimensional acceleration information, along N non-parallel dimensions, corresponding to movement of the individual, wherein N is at least three; and a processor configured to determine, based on the sensor data, a potential injury condition of the individual, said processor being configured to:

project the multi-dimensional acceleration information onto M non-parallel planes thereby generating M projections of acceleration, determine a phasor angle of each of the M projections of acceleration for a sample of sensor data taken within a predetermined window of time, and determine the potential injury condition based on the determined phasor angles within the predetermined window of time.

29. The system according to claim 28, wherein the predetermined window of time is a moving window, and wherein said processor is further configured to update the M projections of acceleration substantially upon receiving a new sample of sensor data.

30. The system according to claim 28, wherein said processor is further configured to generate potential injury condition data corresponding to the potential injury condition.

31. The system according to claim 28, wherein said sensor includes at least one mechanical sensor constructed to measure the multi-dimensional acceleration information.

32. The system according to claim 31, wherein said at least one mechanical sensor is an accelerometer.

33. The system according to claim 32, wherein the multi-dimensional acceleration information contains acceleration data along N non-parallel axes.

34. The system according to claim 33, wherein said accelerometer is arranged to sense acceleration along each of the N axes at predetermined time intervals.

35. The system according to claim 33, wherein each two of the N axes define a two-dimensional plane, such that the N axes collectively define a plurality of two-dimensional planes, and wherein said processor determines the potential injury condition by, for each of at least a portion M of the plurality of two-dimensional planes:

(1) determining a phasor angle of acceleration in the two-dimensional plane during each of the predetermined time intervals within the predetermined time period, and (2) comparing an absolute value of a difference between the smallest phasor angle and the largest phasor angle during the predetermined time period for the two-dimensional plane with a potential injury condition threshold.

36. The system according to claim 35, wherein said processor is further configured to, in the case that the potential injury condition threshold has been exceeded with respect to any one of the M two-dimensional planes, generate a message indicating that the individual is subject to an injury.

37. The system according to claim 35, wherein said processor determines the phasor angle of acceleration in a respective two-dimensional plane defined by, of the N axes, a first axis and a second axis, by:
   determining a ratio of the acceleration along the first axis to the acceleration along the second axis, and
   calculating an inverse tangent of the ratio of the acceleration to determine the phasor angle of acceleration.

38. The system according to claim 35, wherein said processor determines the phasor angle of acceleration by accessing a look-up table.

39. The system according to claim 28, wherein the potential injury condition corresponds to exceeding a potential injury condition threshold associated with either a bend of the knees, a bend of the waist, or a combination of both.

* * * * *